(12) United States Patent
Haase et al.

(10) Patent No.: US 7,181,970 B2
(45) Date of Patent: Feb. 27, 2007

(54) METHOD AND DEVICE FOR TESTING A COMPONENT HAVING A COMPLEX SURFACE CONTOUR BY MEANS OF ULTRASOUND

(75) Inventors: Wolfgang Haase, Sailauf (DE); Gerhard Finger, Limeshain (DE); Roman Koch, Blankenbach (DE)

(73) Assignee: GE Inspection Technologies GmbH, Alzenau (DE)

( * ) Notice: Subject to any disclaimer, the term of this patent is extended or adjusted under 35 U.S.C. 154(b) by 0 days.

(21) Appl. No.: 10/541,313

(22) PCT Filed: Oct. 11, 2004

(86) PCT No.: PCT/EP2004/011331

§ 371 (c)(1),
(2), (4) Date: Jun. 30, 2005

(87) PCT Pub. No.: WO2005/043151

PCT Pub. Date: May 12, 2005

(65) Prior Publication Data

US 2006/0048579 A1   Mar. 9, 2006

(30) Foreign Application Priority Data

Oct. 24, 2003   (DE) ................................ 103 49 948

(51) Int. Cl.
*G01N 29/265* (2006.01)
*G01N 29/06* (2006.01)

(52) U.S. Cl. .......................................... 73/621; 73/633
(58) Field of Classification Search ........... 73/620–961
See application file for complete search history.

(56) References Cited

U.S. PATENT DOCUMENTS 3,555,888 A * 1/1971 Brown ........................ 73/614
3,898,838 A * 8/1975 Connelly ..................... 73/634
4,311,052 A   1/1982 Jeffras et al.
5,335,547 A   8/1994 Nakajima et al.
6,220,099 B1 * 4/2001 Marti et al. ................... 73/633
2003/0192382 A1 * 10/2003 Mueller ...................... 73/620

FOREIGN PATENT DOCUMENTS

DE   69 003090      2/1994
FR      2642833      8/1990
JP       63309852    12/1998
WO    WO 99/41600  * 8/1999

* cited by examiner

*Primary Examiner*—Hezron Williams
*Assistant Examiner*—Rose M. Miller
(74) *Attorney, Agent, or Firm*—Dennison, Schultz & MacDonald

(57) ABSTRACT

A method and a device for testing a structural component having a complex surface contour utilizing ultrasound, at least one ultrasonic head (UPK) being guided along the surface contour (OK) of the structural component (BT) by means of a manipulator (MM) having several axial drives (MX, MJ, MZ, MA, MB) in several axes at a defined spacing (A) along the surface contour (OK) of the structural component (BT). To also ensure a high measuring accuracy in structural components which have a complex curved surface contour, the axial drives (MX, MJ, MZ, MA, MB) of the manipulator (MM) are synchronously moved along predetermined support points, a trigger drive (MRT) is controlled in synchronism with the axial drives (MX, MJ, MZ, MA, MB) and moved together with all engaged axial drives according to a predetermined surface line (OL) reproducing the surface contour (OK) and the trigger drive (MRT) generates equidistant trigger pulses relative to the surface line (OL) of the complex surface contour.

6 Claims, 4 Drawing Sheets

METHOD AND DEVICE FOR TESTING A COMPONENT HAVING A COMPLEX SURFACE CONTOUR BY MEANS OF ULTRASOUND

This application is a filing under 35 USC 371 of PCT/EP2004/011331 filed Oct. 11, 2004.

BACKGROUND OF THE INVENTION

The invention relates to a method of testing a structural component having a complex surface contour by means of ultrasound, at least one ultrasonic head being guided along the surface contour of the structural component by means of a manipulator having several axial drives in several axes at a defined spacing and equidistant pulses being generated as trigger signals for the geometrically correct allocation of received ultrasonic test data for the surface contour of the structural component according to the movement of at least one drive, as well as to a device for testing a structural component having a complex surface contour, comprising a manipulator that displaceable along one or more axes by means of axial drives, at least one ultrasonic head being movable with said manipulator at a defined distance along the surface contour of the structural component, the axial drive being controllable by means of a control and at least one encoder being provided for generating trigger pulses for the geometrically correct allocation of received ultrasonic test data to the surface contour of the structural component.

A method of testing a structural component having a complex surface contour by means of ultrasound is known from an internal state of the art, wherein, on a conventional multiaxial test manipulator, one or more ultrasonic transmitter are arranged which travel along a straight or slightly curved surface contour of a structural component for testing the latter. At least one axial drive of the manipulator is equipped with preferably an optical encoder for generating trigger pulses for an ultrasonic control unit. Each encoder is respectively allocated to a principal axis, such as an X axis. In an automated test of the structural component, the encoder generates equidistant pulses according to the movement of the associated axial drive for a motion vector of the associated axis. The equidistant pulses are necessary as triggers for the geometrically correct allocation of the ultrasonic test data to the test part.

A device 10 having a uniaxial trigger system according to this prior art is shown in FIG. 1. The device 10 comprises a multiaxial manipulator 12, each axis, such as e.g. the X axis, Y axis, Z axis and, perhaps, axes of rotation such as an A axis or B axis, being associated with a drive MX, MY, MZ, MA, MB, controllable by corresponding control cards SX, SY, SZ, SA, SB via a numerically controlled system NCS. One of the axial drives, in the illustrated example the drive MX of the X axis, is coupled with an encoder E which, corresponding to the movement of the associated axial drive, transmits equidistant pulses to an ultrasonic system USS. The trigger pulses are thereby generated in proportion to the advance along the linear X axis. The ultrasonic system USS is coupled with a control computer SR which is, in turn, connected with the numerically controlled system of the multiple manipulator.

If the geometry of the surface contour of the structural component to be tested is curved in a complex manner in the main direction of testing, a sufficient accuracy of the true-to-surface data recordal cannot be guaranteed with a uniaxial triggering. In this sense, true-to-surface data recordal means that an equidistant test point grid on the surface of the structural component is provided as a fixed C image for later reproduction of the measurement results.

A calibration method for a three-dimensional shape-detection system and a system for carrying out that method are described in DE-T 690 03 090. The described calibration method aims to create a new calibration method which is independent of the structure of a sensor unit and, accordingly, does not require a prior physical measurement of geometrical parameters. With the method, the knowledge of the geometric parameters of the sensor unit is replaced by a calibrating object that is easy to dimension. The set-up of an intermediate transfer function takes place directly by detecting the raw information under the same conditions as the later measurement of the points of an object, so that an error accumulation can thus be avoided.

EP-A 0 489 161 relates to an ultrasonic crack detector. Distance sensors and an ultrasonic head are connected to one another as a uniform structure, so that the distance sensor is connected, together with the ultrasonic head, over the scanning lines. The surface scanning of an object W by means of the distance sensor is effected in parallel with the crack detection by the ultrasonic head. The crack detection area is subdivided into a plurality of smaller areas, a plurality of storage areas similar to a net are saved in a storage unit. Only one surface value of the position storage area contains the crack detection area and is stored in each of the storage areas. Based on these stored form data, the position and the angle or position of the ultrasonic head can be controlled in each of the crack detection points.

SUMMARY OF THE INVENTION

Based on this, the object of the invention is to further develop a method and a device of the aforementioned type in such a way that a high measuring accuracy can also be assured for structural components having a complex curved surface contour.

With respect to the method, the object is solved, inter alia, in that the length of a surface line reproducing the surface contour is calculated, that points of support for guiding the ultrasonic head are calculated, that the axial drives of the manipulator are moved synchronously along the predetermined points of support and that a trigger drive is controlled in synchronism with the axial drives and, together with all engaged axial drives, is displaced in accordance with the predetermined surface line, the trigger drive being notionally guided by the surface line and equidistant trigger pulses being generated relative to the surface line.

The basic idea of the method is to ensure a true-to-surface test value allocation, even with structural components having complex curved surface contours, with aid of an additional motor or drive to be moved in a path-synchronous manner with an attached encoder for generating trigger pulses.

In this case, it is provided that a recalculation of a surface line, in particular its length, is calculated according to a geometry of the structural component to be tested, which has been manually input or taken from CAD data. Preferably, the calculation takes place in a control computer of the ultrasonic system. Furthermore, points of support of the multiaxis manipulator for guiding the ultrasonic head system at defined distances along the surface contour of the structural component are calculated in the control computer of the ultrasonic system. In this case, for example, a meander-shaped travel over the surface contour of the structural component is carried out.

When the several drive axes of the multiaxial manipulator travel in a synchronized manner in three dimensions along the predetermined points of support input to the numerically controlled system, the additional motor, as a so-called trigger drive or three-dimensional trigger (virtual axis), synchronized by the numerically controlled system, is then moved, together with all other engaged axial drives, in accordance with the predetermined surface line. As a result of the synchronized travel of the actual axes of rotation to the exact guiding of the ultrasonic head system at a defined spacing along the surface contour of the structural component and the three-dimensional trigger axis, it is ensured that the three-dimensional trigger axis notionally follows the surface line and thus emits equidistant pulses to the ultrasonic system via the attached encoder.

The object is solved by a device in that, in addition to the axial drives, a trigger drive is provided for generating the trigger pulses, that the trigger drive is controlled in synchronism with the axial drives of the manipulator, the axial drives being movable in a synchronous manner along predetermined points of support and the trigger drive, synchronized by the control, being movable together with the axial drives according to a predetermined length of a surface line reproducing the surface contour and that trigger pulses, which are equidistant relative to the surface line of the complex surface contour, are applied to the encoder (E) of the trigger drive.

In addition to the existing axial drives of the multiaxial manipulator, a further axis or a trigger drive is defined, i.e. a motor attached to the numerically controlled system, which is synchronized during the synchronized travel of the axial drives of the multiaxial manipulator in the area along predetermined points of support and is displaced by the together with all other engaged axes, according to the predetermined surface line, so that the trigger drive notionally follows the surface line and thus delivers equidistant pulses to the ultrasonic system via the attached encoder.

BRIEF DESCRIPTION OF THE DRAWINGS

Further details, advantages and features of the invention are found not only in the claims, the features to be found therein—individually and/or in combination—but also in the following description of the preferred exemplary embodiments found in the drawings, in which:

DESCRIPTION OF THE PREFERRED EMBODIMENTS

Figure 1:
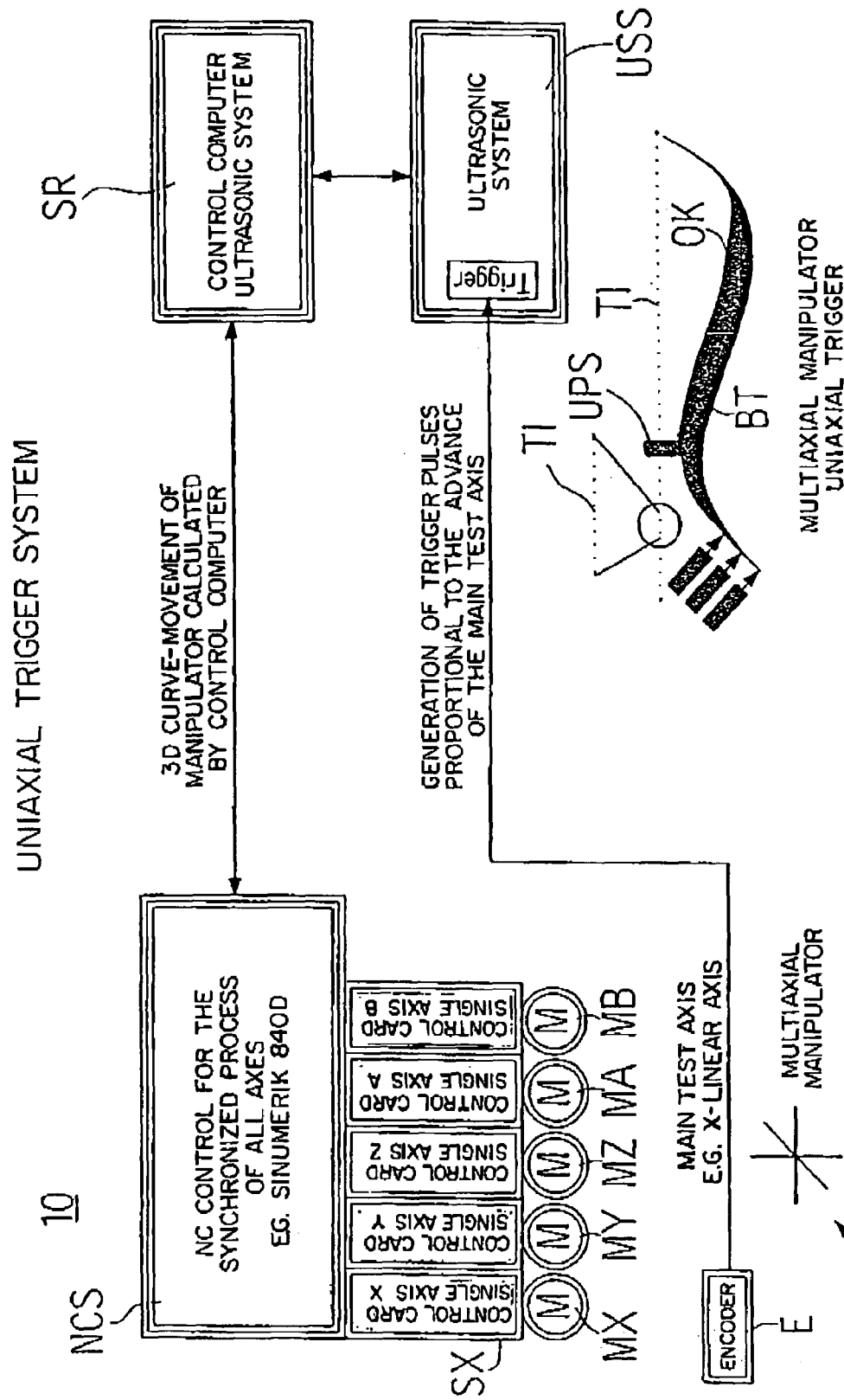
FIG. 1 shows an arrangement for testing a structural component by means of ultrasound with a uniaxial trigger system according to the prior art, FIGS. 2 a, b show basic representations of a manipulator system.

FIG. 1 shows an arrangement 10, for testing a structural component BT having a surface contour OK by means of a uniaxial trigger system, which has already been described in detail in the introduction to the specification.

Figure 2:
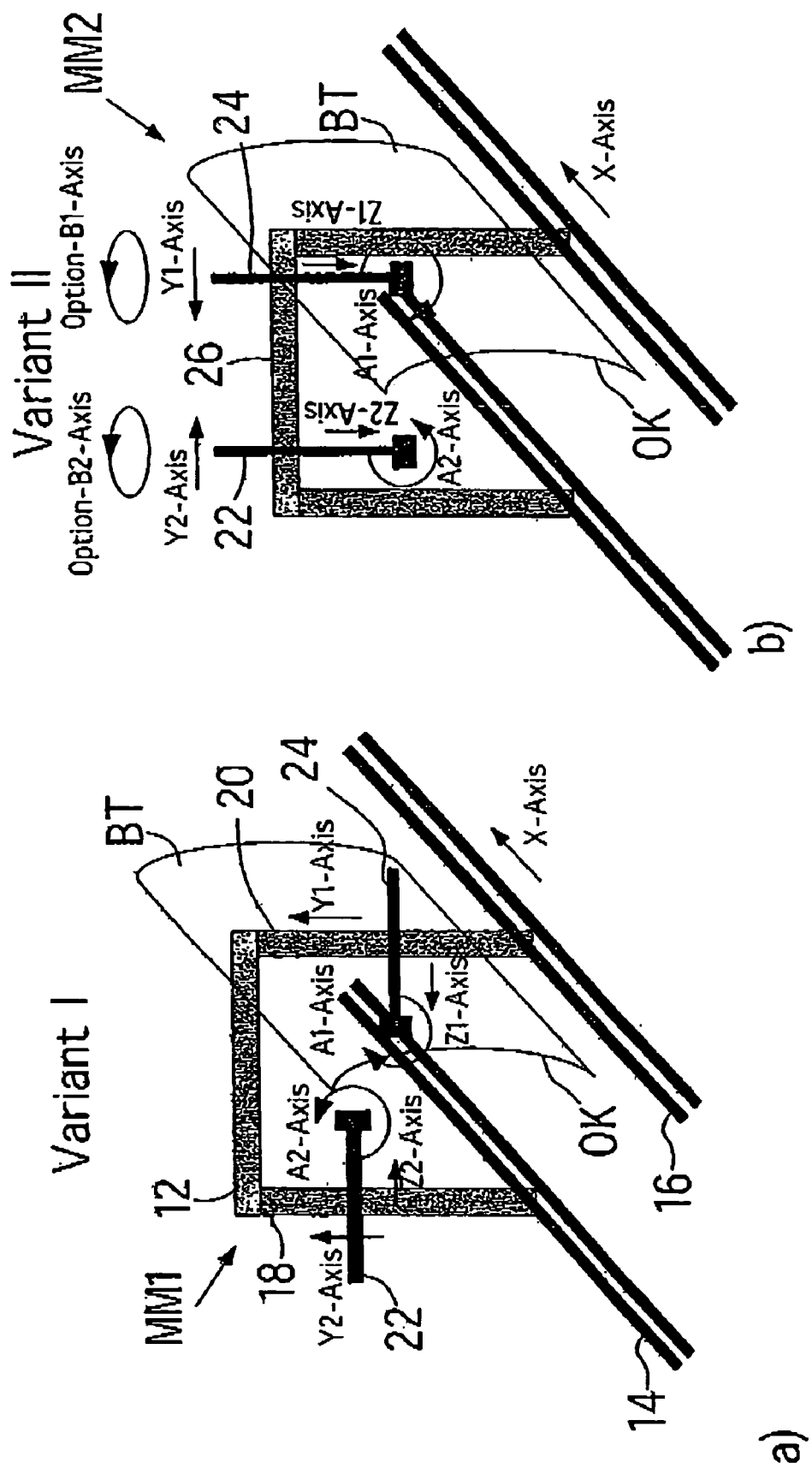

FIGS. 2 a) and b) show two embodiments of the multiaxial manipulator MM for guiding an ultrasonic head system UPS at a defined spacing A along the surface contour OK of the structural component BK. According to a first embodiment, the multiaxial manipulator MM1 comprises an essentially U-shaped frame 12 which is displaceable along guide rails 14, 16 at the bottom along a first axis, such as an X axis, by means of a drive MX. The U-shaped frame thereby essentially surrounds the structural component BT to be tested during travel in the X direction. Holding elements 22, 24 movable along a further axis, such as Y axis, are attached to vertically extending sides 18, 20 of the frame 12 to which the ultrasonic head system UPS is fastened. Furthermore, the holding elements 22, 24 are movable along a further axis, such as the Z axis, in a direction toward and away from the structural component BT to be tested. Furthermore, the ultrasonic head system UPS can be rotated about a longitudinal axis, such as an A axis, of the holding elements 22, 24.

A multiaxial manipulator MM2 shown in FIG. 2 b differs from the manipulator MM1 shown in FIG. 2 a in that the holding elements 22, 24 are not arranged on the vertically extending sides 18, 20 of the frame 12, but are movable along a Y axis of an upper, horizontally extending transverse support 26. Furthermore, the holding elements 22, 24 are movable along a vertically extending Z axis. The ultrasonic head system UPS is, moreover, mounted so as to be pivotable about an A axis. It is optionally provided that the holding elements 22, 24 are pivotable about their longitudinal axis, in the present case about a B axis.

Figure 3:
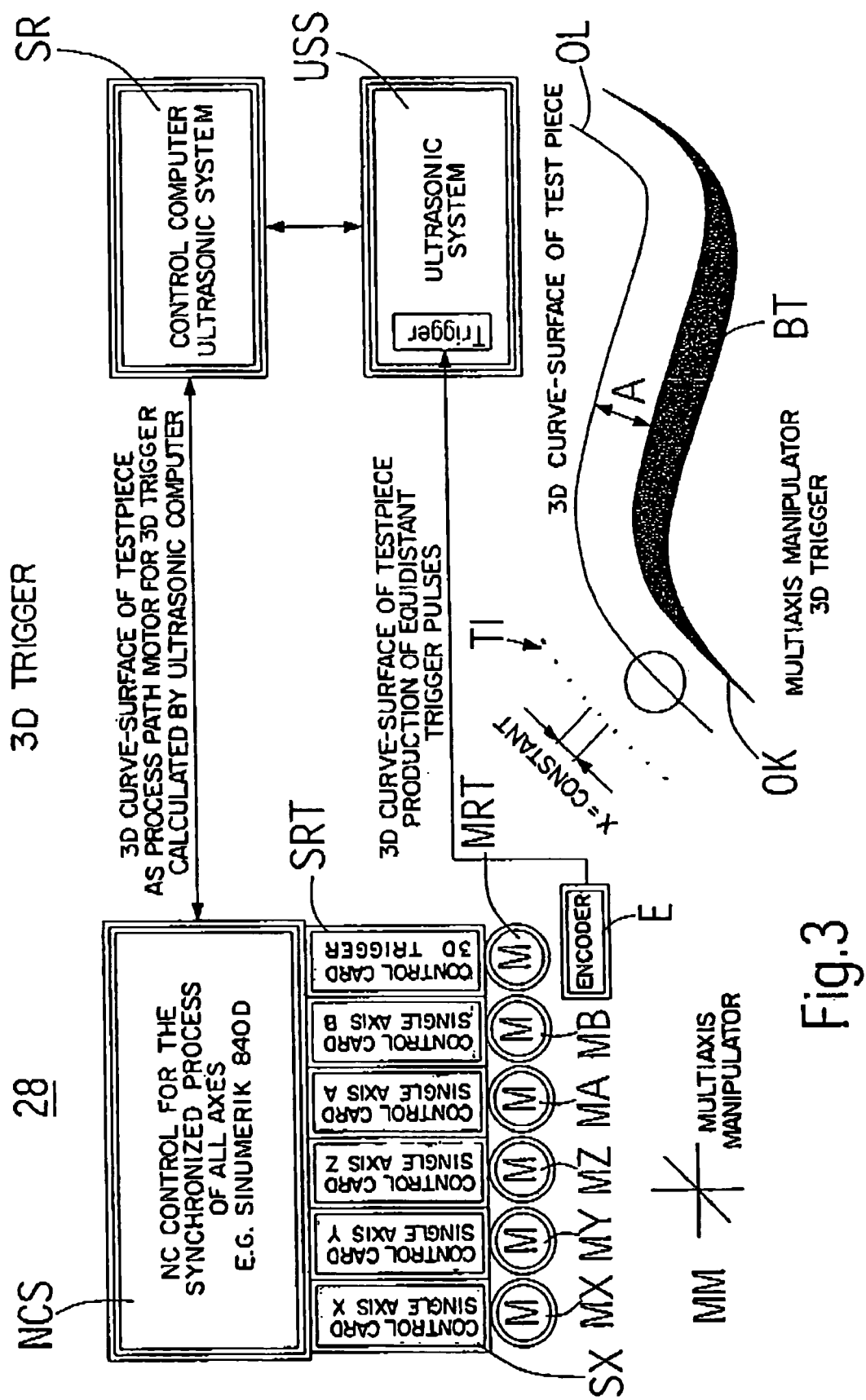
FIG. 3 shows an arrangement for testing a structural component by means of ultrasound with a spatial grid trigger system and FIG. 4 shows a flow diagram with process steps for carrying out the method for testing a structural component having a complex surface contour by means of ultrasound.

FIG. 3 shows an arrangement 28 for testing a structural component BT having a complex surface contour OK by means of ultrasound. The arrangement comprises the multiaxial manipulator MM for guiding the ultrasonic head system UPS at a defined spacing A along the surface contour OK of the structural component. BT. The multiaxial manipulator MM comprises the drives MX, MY, MZ, MA, MB for driving the individual axes, such as the X axis, Y axis, Z axis, A axis and B axis, which are coupled to the control NCS via control cards SX, SY, SZ, SA, SB. According to the invention, a further drive or motor MRT is provided which is connected to the control NCS via a control card SRT. The motor MRT is coupled with an encoder E which delivers trigger signals to an ultrasonic system USS, which is connected to a control computer SR that, in turn, is connected with the control of the multiaxial manipulator NCS.

Figure 4:
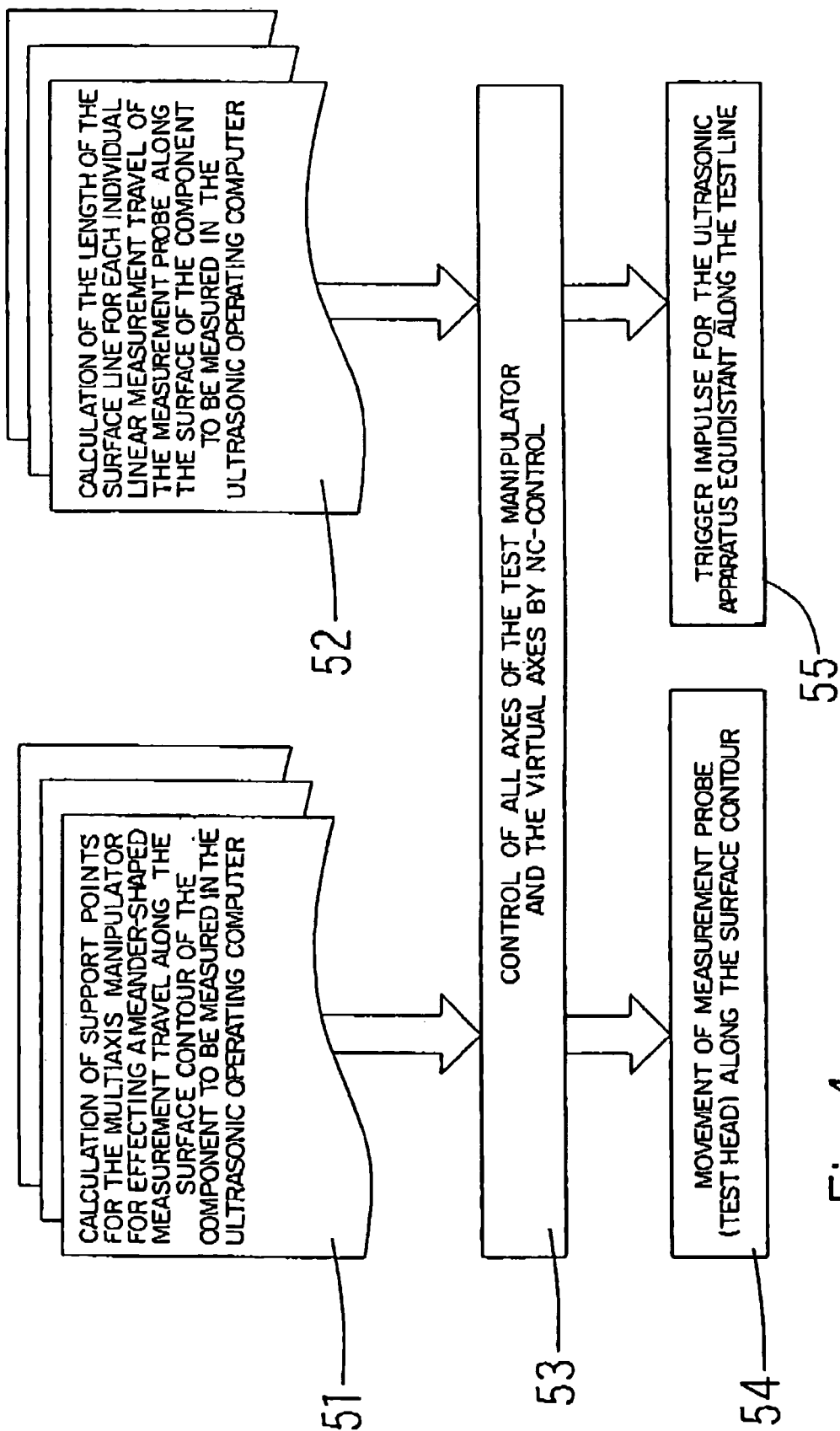

FIG. 4 shows a flow diagram of the method. In the control computer for the ultrasonic system SR, a surface line OL, in particular its length, are calculated from manually input data or from data obtained from a CAD, of the structural component BT to be tested (section S2). Points of support of the multiaxial manipulator MM are then predetermined for guiding the ultrasonic head system UPS at a defined spacing A (section S1). This calculation also takes place in the control computer SR of the ultrasonic system.

Preferably, a meander-shaped measurement travel over the surface contour OK of the structural component BT is carried out. When the axes travel synchronously in three dimensions along the predetermined points of support input into the control NCS, the three-dimensional trigger motor MRT, which can be regarded as a virtual axis, synchronized by the numerically controlled system NCS, together with the other axes which are engaged, is moved in accordance with the predetermined surface line OL (section S3). By the synchronized travel of the actual movement axes, i.e. the X, Y, Z, A and B axes, for the exact guidance of the ultrasonic head system UPS at a defined spacing A along the surface OK and by the travel of the three-dimensional trigger axis of the three-dimensional trigger motor MRT, it is ensured that the three-dimensional trigger axis notionally follows the surface line OL (section S4) and that equidistant pulses T1 are thus delivered to the ultrasonic system USS via the attached encoder E (section S5).

As a result, a sufficient accuracy of the true-to-surface data recordal, i.e. an equidistant test point grid, on the surface of the structural component is ensured for the later representation of the measurement results as a pixelated C image.

What is claimed is:

1. A method of testing a structural component having a complex surface contour by means of ultrasound, comprising the steps of:
    guiding at least one ultrasonic head by means of a manipulator having a plurality axial drives along a plurality of axes at a defined spacing along the surface contour of the structural component,
    according to the movement of at least one drive, generating equidistant pulses as trigger signals for geometrically correct allocation of received ultrasonic test data for the surface contour of the structural component,
    calculating a length of a surface line reproducing the surface contour,
    calculating support points for guiding the ultrasonic head,
    moving the axial drives of the manipulator synchronously along the predetermined support points, and
    controlling a trigger drive in synchronism with the axial drives and, together with all engaged axial drives, displacing the trigger drive in accordance with the predetermined surface line, the trigger drive being notionally guided by the surface line and equidistant trigger pulses being generated relative to the surface line.

2. The method according to claim 1, wherein the length of the surface line is calculated for each individual linear measuring movement of the ultrasonic head along the surface contour of the structural component to be tested.

3. The method according to claim 1, wherein the support points are calculated so as to produce a meander-shaped measurement movement along the surface contour of the structural component to be tested.

4. The method according to claim 1, wherein control of all axial drives and the trigger drive is effected by a numerically controlled system.

5. The method according to claim 1, wherein the trigger pulses are generated for an ultrasonic device guiding the head equidistantly along the surface line.

6. A device for testing a structural component having a complex surface contour, comprising:
    a manipulator movable on one or more axes by means of axial drives,
    at least one ultrasonic head displaceable at a defined spacing along the surface contour of the structural component by means of the manipulator,
    a numerical control system for controlling the axial drives,
    at least one encoder provided for generating trigger pulses for geometrically correct allocation of received ultrasonic test data for the surface contour of the structural part,
    a trigger drive provided for generating the trigger pulses, the trigger drive being controllable in synchronism with the axial drives of the manipulator,
    means for synchronously displacing the axial drives along predetermined support points,
    means for moving the trigger drive, synchronized by the control, together with the axial drives according to a predetermined length of a surface line reproducing the surface contour, and
    means for applying the trigger pulses to the encoder which are equidistant relative to the surface line of the complex surface contour.

* * * * *